US011024998B2

(12) United States Patent
Waterman et al.

(10) Patent No.: US 11,024,998 B2
(45) Date of Patent: Jun. 1, 2021

(54) KIT OF FIRST AND SECOND PARTS ADAPTED FOR CONNECTION TO EACH OTHER

(71) Applicant: Oxford Nanopore Technologies Limited, Oxford (GB)

(72) Inventors: David Waterman, Oxford (GB); Richard Smith, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

(21) Appl. No.: 16/652,013

(22) PCT Filed: Sep. 28, 2017

(86) PCT No.: PCT/GB2017/052910
§ 371 (c)(1),
(2) Date: Mar. 27, 2020

(87) PCT Pub. No.: WO2019/063959
PCT Pub. Date: Apr. 4, 2019

(65) Prior Publication Data
US 2020/0266568 A1   Aug. 20, 2020

Related U.S. Application Data

(63) Continuation of application No. PCT/GB2017/052910, filed on Sep. 28, 2017.

(51) Int. Cl.
*H01R 13/24* (2006.01)
*H01R 13/187* (2006.01)

(52) U.S. Cl.
CPC ....... *H01R 13/2442* (2013.01); *H01R 13/187* (2013.01)

(58) Field of Classification Search
CPC .... H01R 13/2442; H01R 13/24; H01R 13/22; H01R 13/02; H01R 13/187; H01R 13/15
(Continued)

(56) References Cited

U.S. PATENT DOCUMENTS 5,955,028 A * 9/1999 Chow ................. B01L 9/527
                                                              422/63
7,347,715 B2 * 3/2008 Kobayashi ......... H01R 13/4538
                                                              439/248
(Continued)

FOREIGN PATENT DOCUMENTS

WO  WO 2009/077734 A2   6/2009
WO  WO 2014/064443 A2   5/2014
WO  WO 2016/059417 A1   4/2016

OTHER PUBLICATIONS

International Search Report and Written Opinion for Application No. PCT/GB2017/052910 dated Jun. 1, 2018.
(Continued)

*Primary Examiner* — Harshad C Patel
(74) *Attorney, Agent, or Firm* — Wolf, Greenfield & Sacks, P.C.

(57) ABSTRACT

A kit which has a first and second component parts, which are adapted for connection with each other. The first component part has a first array of electrical sensors, two substantially parallel lateral walls on the sides of the electrical connectors, two rails extending along the sides of the array, a front contact point and an overhang for receiving the second part. The second component part has a second array of electrical sensors for connection to the first array, front end configured to fit between the lateral walls of the first connector, and lateral sides having rail reliefs to fit the rails of the first connector. Connection of the first component part and the second component part forms a shoulder that aligns to locate the second array of electrical connectors in correct
(Continued)

position for connection to the first array of electrical connectors.

20 Claims, 11 Drawing Sheets

(58) Field of Classification Search
USPC .......................................................... 439/66
See application file for complete search history.

(56) References Cited

U.S. PATENT DOCUMENTS

| | | | | |
|---|---|---|---|---|
| 7,597,565 | B1* | 10/2009 | Jorgensen | H01R 43/10 439/111 |
| 7,959,474 | B2* | 6/2011 | Beyer | H01R 9/2466 439/712 |
| 8,133,061 | B1* | 3/2012 | Ayers, Sr. | H01R 12/714 439/66 |
| 8,961,201 | B2* | 2/2015 | Griese | H01R 9/2675 439/121 |
| 9,117,614 | B2* | 8/2015 | Rahn | H01R 4/60 |
| 10,549,274 | B2* | 2/2020 | Brown | G01N 33/48721 |
| 2003/0139077 | A1 | 7/2003 | Sasaki et al. | |
| 2014/0125352 | A1* | 5/2014 | Franke | G01R 31/68 324/538 |
| 2014/0164017 | A1* | 6/2014 | Merkin | G16H 40/60 705/3 |
| 2014/0364017 | A1 | 12/2014 | Komoto et al. | |

OTHER PUBLICATIONS

Lu et al., Oxford Nanopore MinION Sequencing and Genome Assembly. Genomics Proteomics Bioinformatics. 2016;14(5):265-279. doi:10.1016/j.gpb.2016.05.004.

Mastrangeli et al., Challenges for Capillary Self-Assembly of Microsystems. IEEE Transactions on Components, Packaging, and Manufacturing Technology. 2011;1(1):133-49.

Mastrangeli et al., Self-assembly from milli- to nanoscales: methods and applications. J Micromech Microeng. Jul. 8, 2009; 19(8): 083001. doi: 10.1088/0960-1317/19/8/083001.

Onoe et al., Three Dimensional Micro-Self-Assembly Using Hydrophobic Interaction Controlled by Self-Assembled Monolayers. J Microelectromech Sys. Aug. 2004;13(4):603-11.

Syms et al., Surface Tension-Powered Self-Assembly of Microstructures—The State-of-the-Art. J Microelectromech Sys. 2003;12(4):387-417.

* cited by examiner

KIT OF FIRST AND SECOND PARTS ADAPTED FOR CONNECTION TO EACH OTHER

RELATED APPLICATIONS

This Application is a national stage filing under 35 U.S.C. 371 of international application number PCT/GB2017/052910, filed Sep. 28, 2017, the contents of which is herein incorporated by reference in its entirety.

The present invention relates to a kit for creating an electrical device with detachable electrical components. The components can be connected to form an electrical connection between the components, and then separated to break the electrical connection and optionally allow the connection to be reformed by reconnecting the components.

A variety of ways of making an electrical connection are known. At small scales, such connections are often made by soldering, as this is a reliable way of ensuring a good connection between two connectors. However, when there is a need to make many connections within a small area, soldering the connections can become difficult. One way of overcoming this difficulty has been to use 'solder bump' or 'flip chip' technology, in which an array of connections on e.g. an integrated circuit are provided with bumps of solder that can subsequently be used to make the necessary connections with e.g. another electrode array.

An example of the usage of the 'solder bump' approach is provided by WO 2009/077734. That patent application discloses an apparatus for creating layers of amphiphilic molecules, and is now briefly discussed with reference to FIGS. 1 and 2.

FIG. 1 shows an apparatus I which may be used to form a layer of amphiphilic molecules. The apparatus 1 includes a body 2 having layered construction comprising a substrate 3 of non-conductive mate ria supporting a further layer 4 also of non-conductive material. A recess 5 is formed in the further layer 4, in particular as an aperture which extends through the further layer 4 to the substrate 3. The apparatus 1 further includes a cover 6 which extends over the body 2. The cover 6 is hollow and defines a chamber 7 which is closed except for an inlet 8 and an outlet 9 each formed by openings through the cover 6. The lowermost wall of the chamber 7 is formed by the further layer 4.

In use aqueous solution 10 is introduced into the chamber 7 and a layer of amphiphilic molecules is formed across the recess 5 separating aqueous solution IO in the recess 5 from the remaining volume of aqueous solution in the chamber 7. Use of a chamber 7 which is closed makes it very easy to flow aqueous solution 10 into and out of the chamber 7. This is done simply by flowing the aqueous solution 10 through the inlet 8. During this process, gas (typically air) in the chamber 7 is displaced by the aqueous solution IO and vented through the outlet 9.

The apparatus includes the following electrode arrangement to allow measurement of electrical signals across the layer of amphiphilic molecules. The substrate 3 has a first conductive layer 20 deposited on the upper surface of the substrate 3 and extending under the further layer 4 to the recess 5. The portion of the first conductive layer 20 underneath the recess 5 constitutes an electrode 21 which also forms the lowermost surface of the recess 5. The first conductive layer 20 extends outside the further layer 4 so that a portion of the first conductive layer 20 is exposed and constitutes a contact 22.

The further layer 4 has a second conductive layer 23 deposited thereon and extending under the cover 6 into the chamber 7, the portion of the second conductive layer 23 inside the chamber 7 constituting an electrode 24. The second conductive layer 23 extends outside the cover 6 so that a portion of the second conductive layer 23 is exposed and constitutes a contact 25. The electrodes 21 and 24 make electrical contact with aqueous solution in the recess 5 and chamber 7. This allows measurement of electrical signals across the layer 11 of amphiphilic molecules by connection of an electrical circuit 26 to the contacts 22 and 25.

The solder bump approach is used in embodiments that have multiple recesses 5, because it is necessary to allow individual electrical connections to the bottom of each well. This is shown in FIG. 2. In FIG. 2, the single conductive layer 20 is replaced with individual conductive paths 28 which extend through the body 2 to a contact 29 on the opposite side of the body 2 from the electrode 21 at the bottom of the recess 5. This arrangement allows for the use of solder bump connections. In particular, deposited on each contact 29 are respective solder humps 60 on which a circuit element 61 can be mounted so that the solder bumps 60 make electrical contact with a track 62 on the circuit element 61.

However, although the solder bump process allows for many electrical connections to be made reliably in close proximity, it suffers from the drawback that the electrical connections formed are permanent.

Other methods for forming permanent electrical connections at small scales are known wherein for example component parts are aligned by self-assembly and subsequently joined mechanical. For example, see "Three Dimensional Micro-Self-Assembly Using Hydrophobic Interaction Controlled by Self-Assembled Monolayers" (Onoe et al., Journal of Microelectromechanical Systems, 2004, Vol. 13, No. 4, pp 603-611); "Challenges for Capillary Self-Assembly of Microsystems" (Mastrangeli et al., IEEE Transactions on Components, Packaging, and Manufacturing Technology, 2011, Vol. 1, No. 1, pp 133-149); "Surface Tension-Powered Self-Assembly of Microstructures—The State-of-the-Art" (Syms et al., Journal of Microelectromechanical Systems, 2003, Vol. 12, No. 4, pp 387-417); and "Self-assembly from milli- to nanoscales: methods and applications" (Mastrangeli et al., Journal of Micromechanics and Microengineering, 2009, Vol. 19, DOT: I0.1088/0960-1317/19/8/083001). However, such techniques often require extreme environments (whether in terms of chemical activation, or in terms of system variables such as temperature or pressure), which may not be suitable for electrical devices with sensitive components and also provide permanent electrical connections.

A method of making a non-permanent electrical connections is discussed in WO 2016/059417. That document provides an array of electrical connections between component parts of an electrical device in such a way that the component parts can be attached and detached, and optionally reattached thereafter, without requiring extreme conditions (whether chemical or environmental) to trigger the connection or disconnection.

By using an array of electrical connectors comprising an electrically conductive liquid, an array of connections can be made without requiring extreme conditions or pressure which could potentially damage a sensitive electrical device, or component part thereof. FIG. 3 illustrates this concept, and shows two bodies 32 and 37 which represent component parts of an electrical device 31. An array of capillaries 34 is formed in the body 32. The capillaries 34 extend from one surface of the body 32 to the other, and are filled with an electrically conductive liquid. The liquid filled capillaries form electrical connectors 35. As illustrated in FIG. 3, the liquid connector 35 may project from the surface facing the other component forming the electrical device 31 (i.e. the lower surface of the body 32 in FIG. 3), to assist with providing a good electrical connection. This allows a good connection with electrodes 38 to be made when bodies 32 and 37 are brought into contact. In some embodiments an electrical device further comprises one or more of each of the following: a well wall 33, a well recess 36, and/or a suitable analysis unit 51.

However, the use of liquid connectors as set out in WO 2016/059417 has practical limitation in terms of storing the component parts and maintaining the quality of the liquid connectors during manufacture and transport, as well as in eventual use Therefore, it is an object of the present invention to at least partially overcome the problems discussed above.

According to a first aspect of the invention there is provided a kit comprising first and second component parts adapted for connection to each other, wherein: the first component part comprises one or more of: a first array of electrical connectors; two substantially parallel lateral walls, one provided on either side of the first array of electrical connectors at a predetermined position with respect to the first array of electrical connectors; two rails provided between the first array of electrical connectors and the lateral walls, one rail being on either side of the first array of electrical connectors, wherein each rails extends at least along a length of the first array of electrical connectors, and has a front tip positioned at a predetermined position with respect to the first array of electrical connectors; a front contact point; an overhang for receiving the second component; the second component part comprises one or more of: a second array of electrical connectors, for connection to the first array of electrical connectors; a front end being configured to fit to a width between the parallel lateral walls, lateral sides, each comprising a rail relief to allow the sides to fit around the two rails, and wherein a shoulder is formed by the front end of each rail relief; and wherein the first and second components are configured such that they may be connected by sliding the front end of the second component along the two rails of the first component and under the overhang, so that the shoulders of the rail reliefs of the second component pass the from tips of the rails of the first component, and the front end of the second component bears against the front contact point of the first component, urging the shoulders of the rail reliefs against the front tips of the rails, thereby locating the second array of electrical connectors in the correct position for connecting to the first array of electrical connectors.

According to this aspect, the two arrays of connectors can be aligned, connected, and disconnected accurately and repeatably. This is achieved by providing corresponding datum surfaces at predetermined positions on the two components, and the construction ensures those datum surfaces are brought into proper contact.

In some embodiments the rails of the first component project above the first array of electrical connectors, such that the second component cannot be brought into contact with the first array of connectors until the first and second arrays of connectors are aligned in the correct position for connecting. This helps protect the first array from contact with parts of the second component not intended to connect to the first array, and therefore reduces the chances of the first array being damaged during the connection (or disconnection) process. It also reduces the chance of damaging the first and/or second array of connectors as a result of sliding the second set over the first set of connectors.

In some embodiments the front end of the second component comprises a front spring. In some embodiments the front spring of the second component is provided by a flexible portion of the front end of the second component. In some embodiments the front contact point of the first component comprises a pip for the front spring of the second component to bear against. In these embodiments, the spring on the second component bears against the first component to push the second component, and thus the second array, into the correct position for connecting to the first component and the first array.

In other embodiments the front wall of the first component comprises a front spring. In these embodiments, the spring on the first component bears against the second component to push the second component, and thus the second array, into the correct position for connecting to the first component and the first array.

In some embodiments the width of the front and back ends of the second component is smaller than the width between the parallel lateral walls by up to half a pitch between electrical connectors of the first array of electrical connectors. This ensures that the two arrays of connectors can be aligned correctly in the direction of width, without connectors in one array crossing into contact with connectors adjacent to the intended corresponding connectors in the other array.

In some embodiments the front and/or back ends of the second component are compressible to fit within the width between the parallel lateral walls. This can make use of elastic averaging to ensure that the two arrays are brought into the correct alignment across the width of the components.

In some embodiments the overhang is a spring. This helps push the two components together and ensure a good connection.

In some embodiments the first component part has first and second sub-parts, the first and second sub-parts being separable from each other. In some embodiments the first sub-part comprises the overhang, and the second sub-part comprises the two substantially parallel lateral walls, the two rails provided between the first array of electrical connectors and the lateral walls, and the front contact point. In some embodiments the second sub-part comprises a canopy for fitting against the overhang of the first sub-part. In these arrangements, one sub-part can effectively net as an adaptor for fitting a re-usable or replaceable second component to the first component.

In some embodiments the first array of electrical connectors is raised from a surface of the first component, so as to act as a fulcrum over for the second component. This can help ensure that the connectors of the two arrays are brought into contact with sufficient force to ensure a good quality connection.

In some embodiments the first or second component comprises a latch configured to hold down the back end of the second component, to hold the first and second components in a connected configuration. In some embodiments the overhang, the latch, and the first array of electrical connectors act in combination to bend the second component when it is held in the connected configuration.

In some embodiments the front end of the second component further comprises a flexible cantilever for fitting under the overhang of the first component.

According to another aspect of the invention, there is provided method for connecting first and second component parts to each other, wherein: the first component part comprises one or more of: a first array of electrical connectors; two substantially parallel lateral walls, one provided on either side of the first array of electrical connectors at a predetermined position with respect to the first array of electrical connectors; two rails provided between the first array of electrical connectors and the lateral walls, one rail being on either side of the first array of electrical connectors, wherein each rails extends at least along a length of the first array of electrical connectors, and has a front tip positioned at a predetermined position with respect to the first array of electrical connectors; a front contact point; an overhang for receiving the second component part; the second component part comprises one or more of: a second array of electrical connectors, for connection to the first array of electrical connectors; front and back ends being configured to fit to a width between the parallel lateral walk, lateral sides, each comprising a rail relief to allow the sides to lit around the two rails, and wherein a shoulder is formed by the front end of each rail relief; and the method comprises one or more of: sliding the front end of the second component beyond the front tips of the two rails of the first component and under the overhang; pressing the front end of the second component against the front contact point of the first component, so that either the front end or the front contact point undergoes compression, thereby passing the shoulders of the rail reliefs of the second component beyond the front tips of the rails of the first component; allowing the compression in the front end or the front contact point to urge the shoulders of the rail relief against the front tips of the rails, thereby locating the second array of electrical connectors in the correct position for connecting to the first array of electrical connectors.

In some embodiments the mils of the first component project above the first array of electrical connectors, such that the second component is prevented from contacting the first array of connectors during the sliding step, until the first and second arrays of connectors are aligned in the correct position for connecting.

In some embodiments the front end of the second component, or the front contact point, comprises a front spring.

In some embodiments the method further comprises compressing the front and/or back ends of the second component to fit within the width between the parallel lateral walls.

In some embodiments the method further comprises restraining the back end of the second component, to hold the first and second components in a connected configuration. In some embodiments the restraining causes the second component to bend.

In some embodiments, the front end of the second component further comprises a flexible cantilever for fitting under the overhang of the first component, and the method further comprises deflecting the cantilever against the underside of the overhang, after sliding the front end of the second component under the overhang, as the hack end of the second component is restrained to hold the first and second components in a connected configuration. In some embodiments the method further comprises releasing the restraint on the back end of the second component, and allowing the cantilever to return to an undeflected position.

The invention is discussed below, by way of example only, with reference to the following figures in which.

The inventors have devised a way of providing an array of electrical connections between component parts of an electrical device in such a way that the component parts can be attached and detached, and optionally reattached thereafter, without requiring extreme conditions (whether chemical or environmental) to trigger the connection or disconnection, and without requiring inordinate care by the user to ensure that the connectors are not damaged. This is of particular use in connecting elements of a nanopore analysis device, of the types discussed in WO 2016/059417.

In typical prior art electrode arrays such as those disclosed by WO 2014/064443, test cartridge or flow cell for receiving a test solution is provided comprising an array of nanopores supported in an array of wells, each well having an electrode at its base. The structure may be formed for example by UV photolithography of the array structure onto a silicon chip comprising the array of electrodes on the surface of the chip and connected to the underside of the chip by vias to an application-specific integrated circuit (ASIC). The well array structure and silicon chip is formed as one disposable component meaning that alter use it either needs to be disposed or cleaned prior to reuse. Disposal is undesirable due to the cost of the chip whereas cleaning and reuse is undesirable due to the potential for contamination. Therefore it is desirable to have a device wherein, the well array structure is not formed as a single component with the silicon chip and which may be physically connected to an electrode array. In this way the silicon chip, which is the more expensive component may be detached from the well array component and reused.

Figure 1:
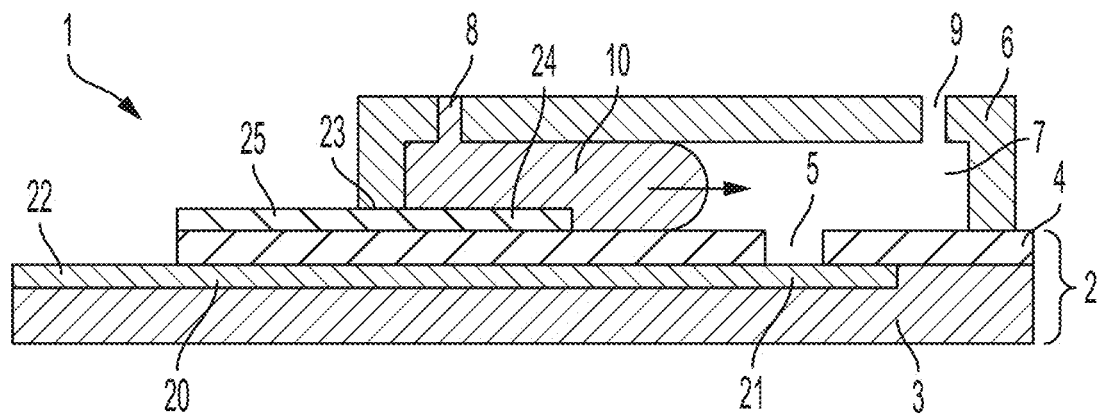
FIG. 1 is a cross sectional view of a prior art apparatus.
Figure 2:
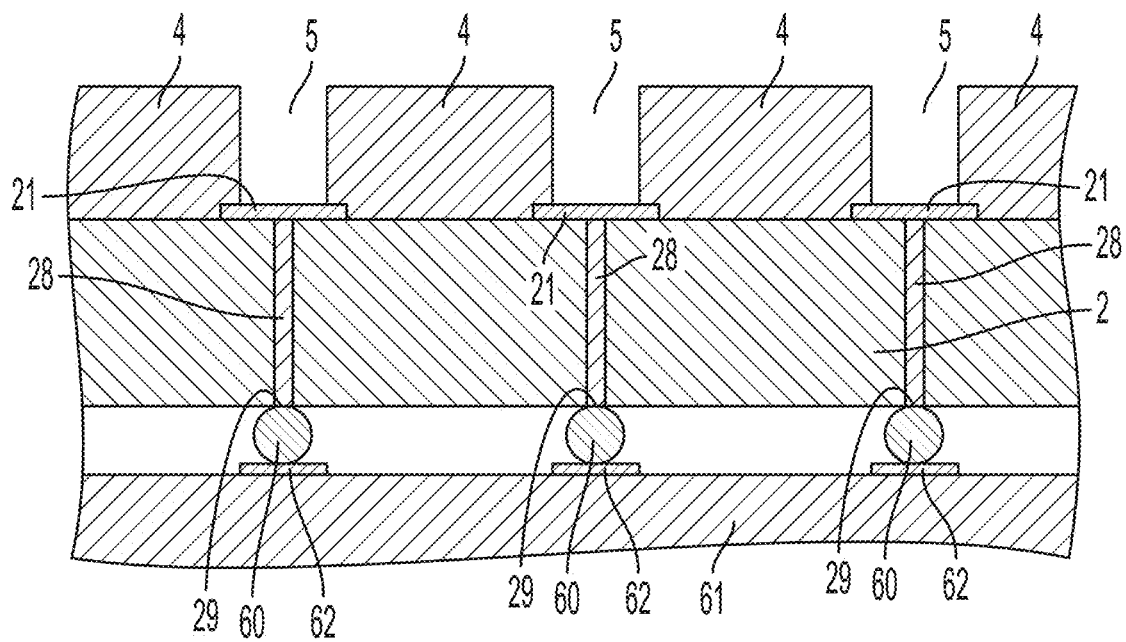
FIG. 2 is a cross sectional view of a prior art apparatus.
Figure 3:
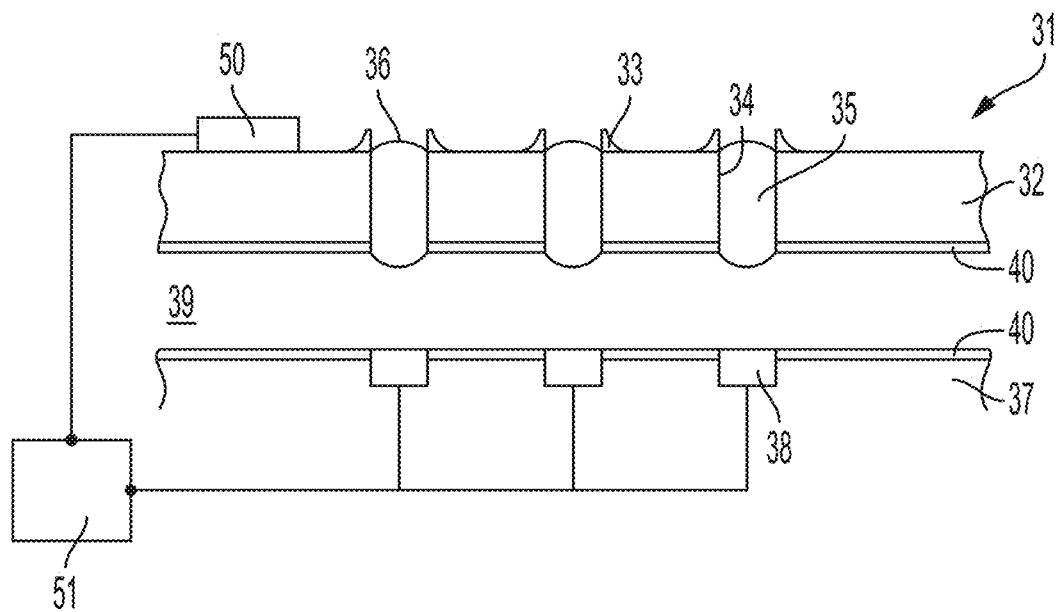
FIG. 3 is a cross sectional view of a prior art electrical device, with two component bodies separated from, but connectable to, each other.
Figure 4:
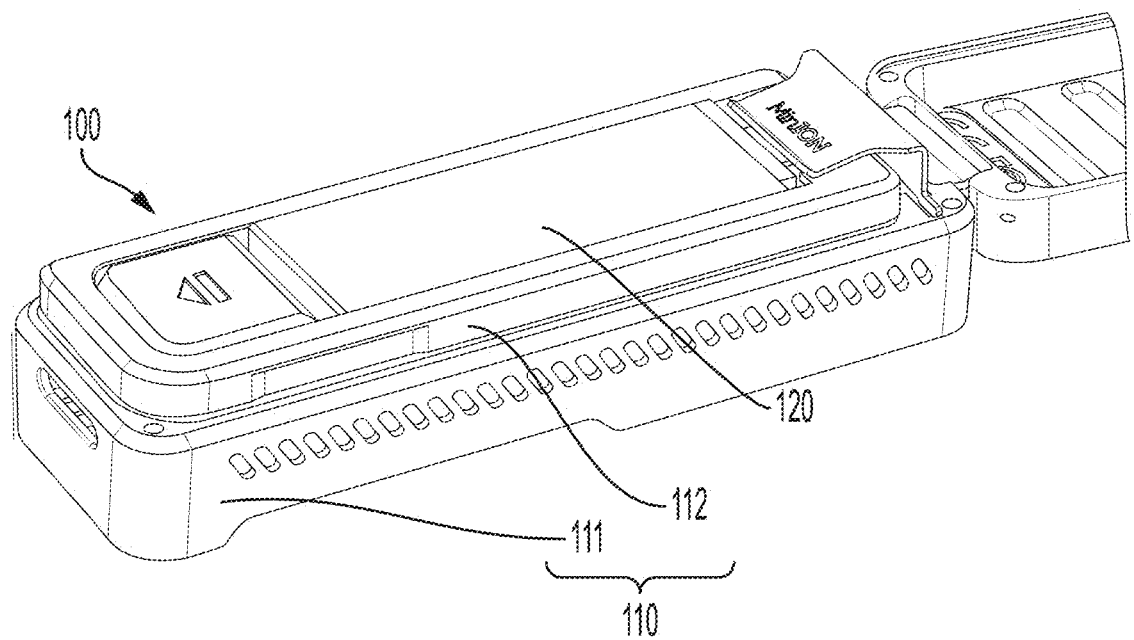
FIG. 4 is a perspective view of a device formed from a kit of constituent components that have been connected together.

FIG. 4 shows an apparatus 100 which may be used to form a layer of amphiphilic molecules, similar to that of FIGS. 1 and 2. However, the apparatus 100 of FIG. 4 is made of detachable components. As such, the constituent components of apparatus 100 may be provided as a kit.

A first component 110 forms the base of the device 100, whilst a second component 120 can be inserted and removed from the base component 110. When inserted, the first and second components 110, 120 form a connection between first and second arrays of electrical connectors (discussed further below). This allows multiple second components to be used with a single base component 110. The body of the second component is typically made of a plastic material having a degree of elasticity. The plastic material may for example be polycarbonate.

In the example device of FIG. 4, a disposable flow-cell is provided as the second component 120. The flow cell can be equivalent to that discussed in WO 2014/064443, which is hereby incorporated in its entirety by reference. In the arrangement of FIG. 4, the ability to provide a disposable flow-cell 120 means that more expensive components of the analysis device 100 can be incorporated into the first component 110, making it possible to perform multiple experiments with different flow-cells 120 relatively cheaply. As such, the flow-cell 120 may comprise corresponding features to the recesses and apertures 5 described in respect of FIG. 1 and FIG. 2. Meanwhile, for example, the circuit element 61 and track 62 illustrated in FIG. 2 can be provided in the base section 110.

The base component 110 can further comprise, as illustrated, subcomponents 111, 112. In this example, and as discussed further below, the first sub-component 111 comprises the electronics and cooling configuration for the overall device 100. The second sub-component 112 acts as an adaptor to fit a second component 120 to the first sub-component 111. In particular, the adaptor sub-component 112 can incorporate further electronics not provided in the base component 110, but which it is desirable to keep separate from the second component 120. This might be, for example, to reduce the cost (and thus increase the disposability) of the second component 120, without further complicating the base component 110. In any case, the precise purpose of each of the components and sub-components is not essential. Indeed, in other arrangements, the sub-components 111 and 112 may be integrally formed as a single base component 110.

Figure 5:
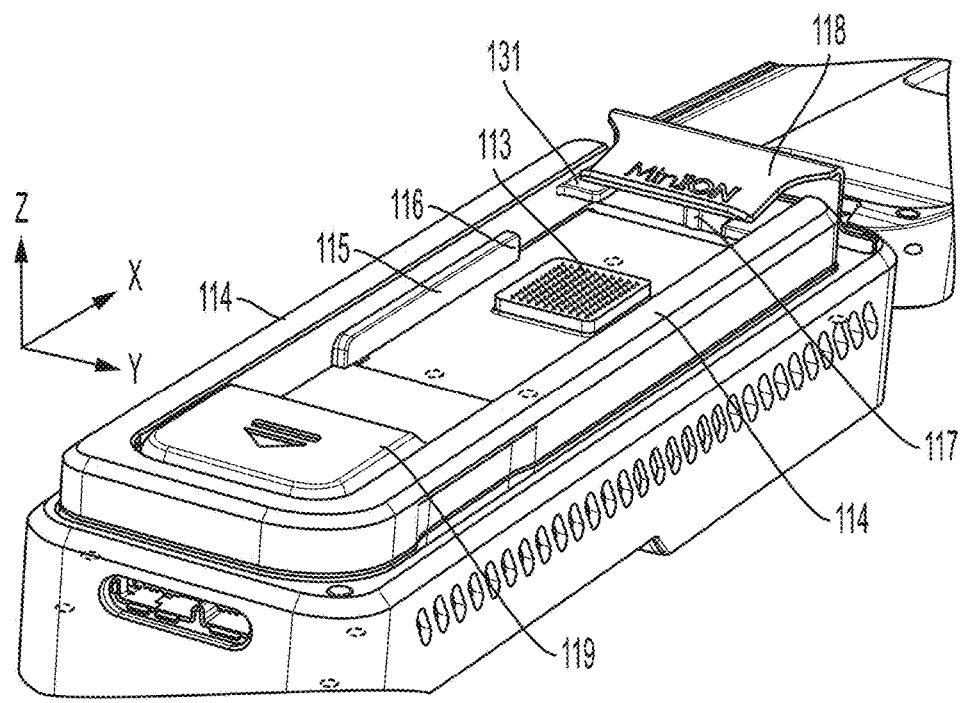
FIG. 5 is a perspective view of the base component of FIG. 4.

FIG. 5 shows further detail of the base component 110, with the flow-cell 120 removed. The removal of flow-cell 120 reveals the first array of electrical connectors 113. This array 113 connects to a corresponding array on the underside of the flow-cell 120, as discussed later. The base component 110 (in particular, the first sub-pan 111 in this arrangement), is provided with two substantially parallel lateral walls 114, forming the lateral boundaries around an inner cavity. In some embodiments, the presence of the lateral walls 114 may not be necessary, or the walls 114 not be continuous. The lateral walls 114 are provided on either side of the first array of electrical connectors 113, at a predetermined position with respect to the first array of electrical connectors. The predetermined position aids the connection of the first and second arrays 113, 123 as discussed below. Each electrical connector 123 is intended to contact a respective connector of array 113. The pitch between the connectors may be typically a value between 400 and 1600 um. The connectors are metallic and typically made from an inert metal such as gold or platinum.

Two rails 115 are provided between the first array of electrical connectors 113 and the lateral walls 114. That is, me rail 115 is provided on either side of the first array of electrical connectors 113, between the first array of electrical connectors 113 and one of the lateral walls 114. Each rail extends at least along the length of the first array of electrical connectors 113. This is because the rails 115 act as a guide for inserting the flow-cell component 120 as discussed in more detail later. As such, the rails 115 act to keep the flow-cell 120 above the first array of electrical connectors 113, without allowing the flow-cell component 120 to touch the first array of electrical connectors 113, as the flow-cell component 120 is slid along the rails 115 to be positioned for connection. To assist with this, the rails 115 can project further above the surface of the base component 110 than the first array 113.

Each rail 115 has a front tip 116, which is positioned at a predetermined position with respect to the first array of electrical connectors 113. The predetermined position aids the connection of the first and second arrays 113, 123 as discussed below. In use, as the flow-cell component 120 is slid along the rails 115, the front tips 116 represent the point at which a front end of the flow-cell component 120 can slip down beyond the rails 115 and the first array of electrical connectors 113.

In other arrangements the rails 115 could be provided on the flow-cell component 120, with gulleys in the base component 110 to receive the rails at the correct position.

At a front part of the base component 110 (the front being the end into which the flow-cell component 120 is first located, when connecting the two components 110, 120), there is provided a front contact point 117. The front contact point 117 is the point against which the front end of flow-cell component 120 bears as it is inserted (see further discussion below). In the particular example illustrated, the front contact point 117 comprises a "pip" or "bump" on the end wall of the base component 110. However, any other form of contact point is acceptable. As discussed further below, the contact point may not necessarily be a fixed point but may be a compressible point such as a spring.

The base component 110 further comprises a clip or overhang 118 for receiving the flow-cell component 120 at the front end. The overhang 118 can be sprung, so that it can be displaced from its resting position by the insertion of the flow-cell component 120 (see discussion below) and subsequently bear against the flow-cell component 120. The benefit of providing a sprung overhang 118 is that this allows for larger tolerances, and therefore reduced manufacturing cost/difficulty, in connection with correctly locating the two components 110, 120 in the z-direction. In the embodiment illustrated, dip 118 forms part of the first sub-component of the base component 110. In this example, as well as constraining the flow-cell component 120 as discussed in more detail below, the clip also bears against canopy sections 131 of the second sub-component 120, ensuring that the two sub components 111, 112 are firmly held together. This is also assisted by the clip 118 being sprung.

At the other end of the base component 110 (i.e. the back end) there is provided a latch 119. The latch is configured to restrain the back end of the flow-cell component 120, after it has been inserted, to hold (in combination with the clip 118) the two components 110, 120 in a connected configuration. Once the back end of the flow-cell component 120 has been pushed past the latch 119, it will bear back up against the underside of the latch 119, until the latch 119 is released. The latch 119 can also act as an "eject" button to release the flow-cell component 120 from the base component 110, when needed (see discussion below).

Figure 6:
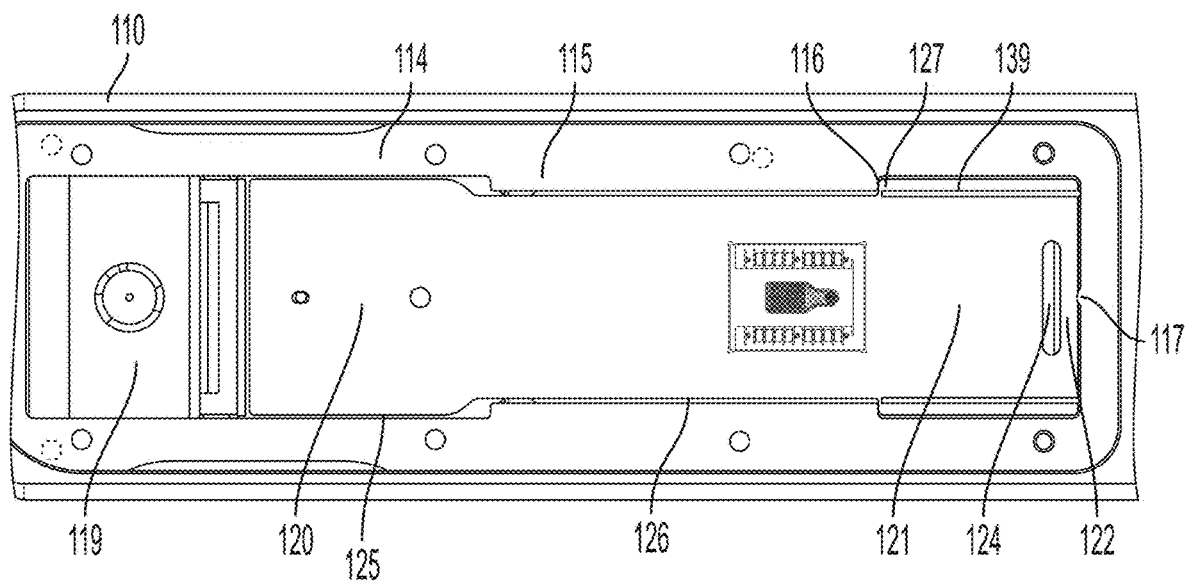
FIG. 6 is a cross-sectional plan view through two connected components.

FIG. 6 illustrates how flow-cell component 120 fits within the base component 110, showing a cross-section through the base component 110 (i.e. so the clip 118 and the canopies 131 are not visible).

As can be seen, the flow-cell component 120 has a front end 121 which contacts the front contact point 117 of the base component 110. The front end 121 of the flow-cell component 120 comprises a hole 124. This allows a section of the front end 121, beyond the hole 124, to act as a spring 122. In other words, spring portion 122 is flexible, and can flex against the front wall contact point 117, by virtue of the hole 124 provided behind it.

The lateral sides 125 of flow-cell component 120 fit within the walls 114 of the base component 110. In addition, the flow-cell 120 has a rail relief 126 on each lateral side 125. Each rail relief 126, when the flow-cell component 120 is in the connected configuration, fit around a rail 115 of the base component. In other words, a width of the flow-cell component 120 between the rail reliefs 126 is narrower than the width between the rails 115. In contrast, the front end 121 of the flow-cell component 120 is wider than the space between the rails 115. As a result, the flow-cell component 120 cannot be pushed into the connected position within the base component 110 until the front end 121 has passed beyond the rails 115 and under the clip 118.

The provision of the rail reliefs 126 results in shoulders 127 being formed at the junction between the front end 121 and the rail reliefs 126. In other words, each shoulder is formed at the front end of the rail relief 126.

As can be seen in FIG. 6, the shoulders 127 sit next to front tips 116 of the rails 115 in the connected configuration. In fact, the shoulders 127 are urged against the front tips 116 by the spring 122. By positioning the front tips 116 of the rails 115 at a predetermined position with respect to the first array of electrical connectors, and by similarly providing the shoulders 127 of the flow-cell component 120 at a predetermined position with respect to the second array of electrical connectors 123 (provided on the base of the flow-cell component 120, and for connection to the first array of electrical connectors 113), the two arrays 113, 123 can be correctly located with respect to each other in the x direction as shown in FIG. 1, i.e. In the direction extending from the front to the back of the apparatus 100.

Figure 7:
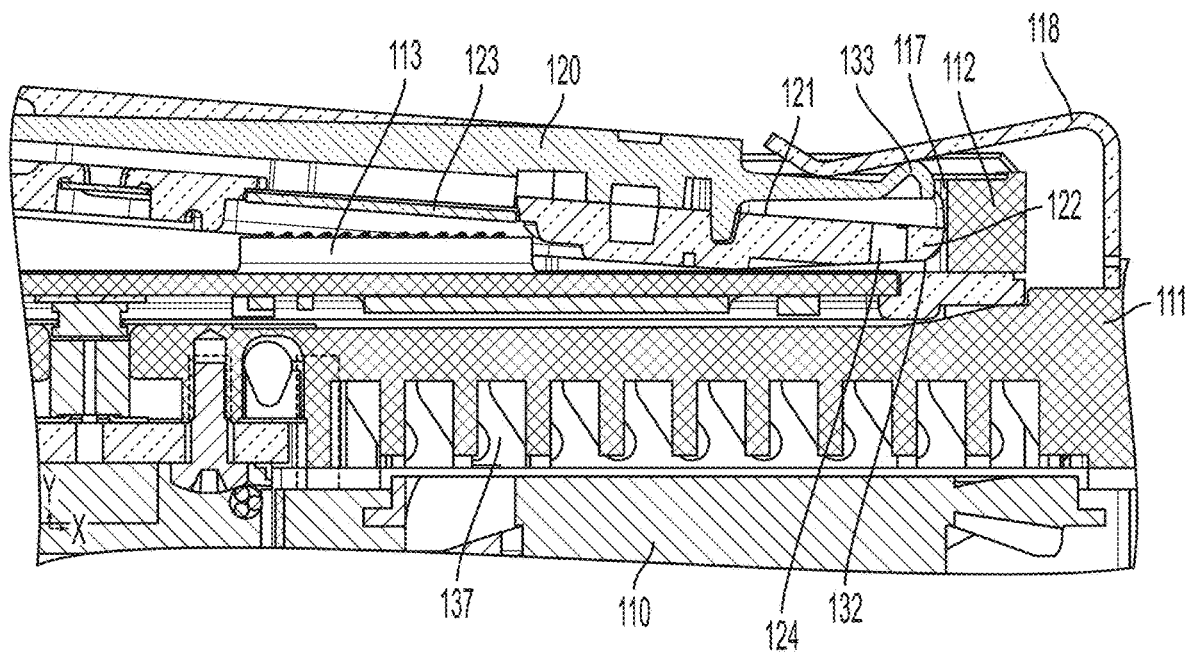
FIG. 7 is a cross-sectional side through the front end of two components in the process of being connected.
Figure 9:
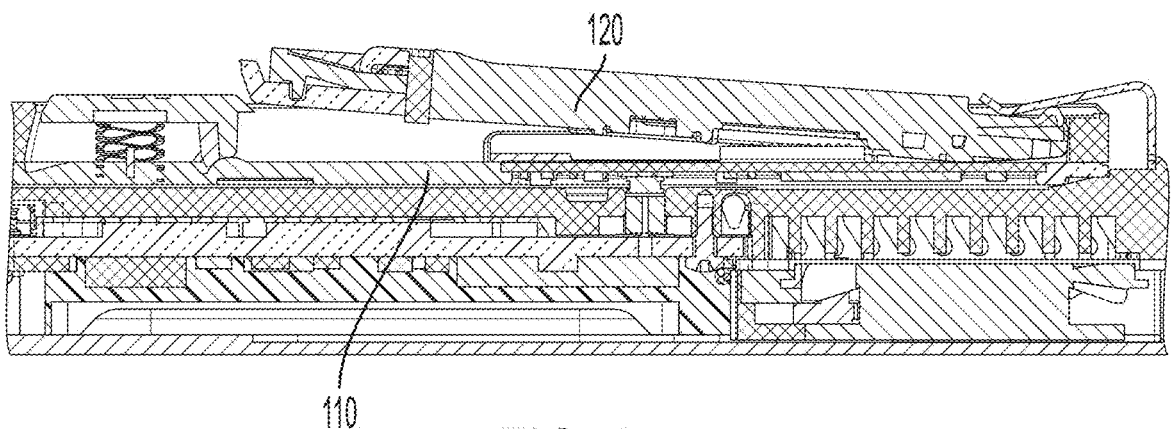
FIG. 9 is a cross-sectional side through the two components being connected.
Figure 10:
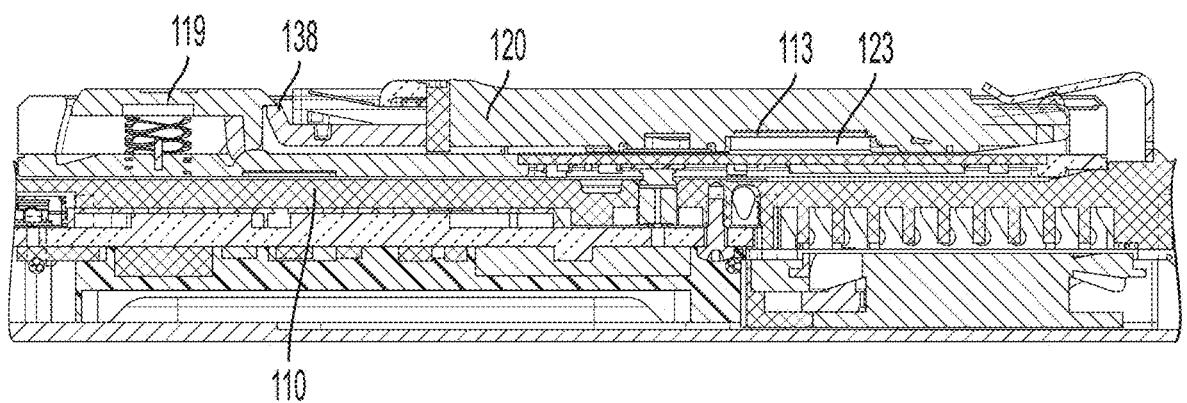
FIG. 10 is a cross-sectional side through the front end of two components in a connected configuration.

FIGS. 7, 9 and 10 show how the flow-cell component 120 comes into position for connecting the first and second arrays of electrical connectors 113, 123. FIG. 7 shows a close view of the front end of the flow-cell component 120 as it is inserted in the base component 110. FIG. 9 shows a view of the whole flow-cell component 120 as it is inserted in the base component 110. FIG. 10 shows a view of the whole flow-cell component 120 in a connected configuration with the base component 110.

As shown in FIG. 7, the front end 121 of the flow-cell component 120 has passed beyond the rails 115 of the base component 110, and fits under clip 118. As can be seen in FIG. 7, the front end 121 can have a taper, bevel or chamfer 132, to help encourage it to slip under the clip 118 whilst the back end of the flow-cell component 120 is still raised. That is the tapering 132 of the front end 121 causes a reduction in depth of the flow-cell component 120 towards the front end 121 that facilitates the insertion of the flow-cell component into the base component 110 under the clip/overhang 118.

The rear-ward point at which the taper 132 ends can also provide a pivot point about which the flow-cell can be pivoted as the back end is pushed down, urging the front end 121 against the underside of the overhang 118. If the overhang 118 is sprung, this can cause the overhang to deflect away from its resting positions, and thus be back against the front end 121 of the flow-cell component 120, holding it in place. When the back end of the flow-cell component 120 is pushed down far enough, the point at which the taper ends can be lifted away from the base component 120, and therefore cease to act as a pivot, if the first array 113 is raised to act as a fulcrum (as discussed below).

The front end 121 also has a flexible cantilever portion 133 with a lip that projects up and into contact with the clip 118. When the base component 110 is provided as two sub-components 111, 112 in the manner of FIG. 5, the lip of cantilever portion 133 projects upwards between the canopies 131 of the second sub-component 112, so as to contact clip 118, As such, the angled clip 118 bears down on the upper surface of the front end 121 of the flow-cell component 120, whilst cantilever 133 bears upwards against the underside of the clip 118. Both cantilever 133 and clip 118 can flex as the two parts bear against each other. In other implementations, only of the cantilever 133 or clip 118 might flex.

Figure 8:
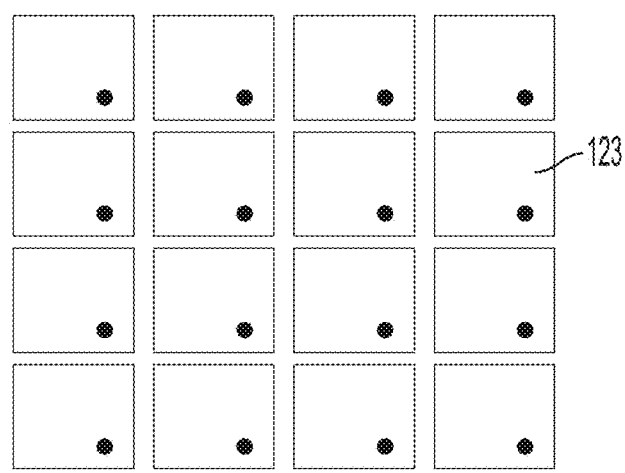
FIG. 8 shows an array of connectors.

When the front end 121 of the flow-cell component 120 has been inserted fully, the spring 122 comes into contact with the front wall contact 117, and the shoulders 127 the flow-cell component 120 can pass the rail tips 116. In that configuration, the back end of the flow-cell component 120 can be pressed down, allowing the lateral rail reliefs 126 to pass around the rails 115 and bringing the first and second arrays of electrical connectors 113, 123 together into a connected configuration. In the connected configuration, each connector of the first array 113 connects to a corresponding connector of the second array 123. The second electrode array 123 is positioned on the underside of the flow-cell component 120, and is illustrated in FIG. 8.

In other words, the base component 110 and the flow-cell component 120 are configured such that they may be connected by sliding the front end 121 of the flow-cell component 120 along the two rails 115 of the base component 110 and under the overhang 118, so that the shoulders 127 of the rail reliefs 126 of the flow-cell component pass the front tips 116 of the rails 115 of the base component 110, and the front end 121 of the flow-cell component 120 bears against the front contact point 117 of the base component 110, urging the shoulders 127 of the rail reliefs 126 against the front tips 116 of the rails 115, thereby locating be second array of electrical connectors 123 in the correct position for connecting to the first array of electrical connectors 113.

The back end of the flow-cell component 120 can include a latch surface 138, against which the latch component 119 bears once the components 110, 120 are in the connected configuration. Once the latch 119 has been engaged, the front end 121 is held in place by the clip 118 and the back end is held in place by the latch 119. The clip 118 and the latch 119 act to hold the first and second array of electrical connectors 113, 123 in electrical connection (i.e. they provide a connecting force in the z direction of FIG. 1). The amount of force applied in the z direction across the connectors can be in the range of 15 g/pin to 40 g/pin, for example 31 g/pin. Thus in order to make reliable connections across the array, a considerable amount of three may need to be applied especially when the number of connectors that need to be connected is large. The number of connectors in each array may typically be anywhere between 100 and 5000. The spring forces, for example the spring force of clip 118, may be varied accordingly depending upon the force required to reliably make electrical connections between the two arrays of connectors.

In some embodiments, the first array of electrical connectors 113 is raised with respect to the surrounding surface of the first component 110. This allows for the first array of electrical connectors 113 to act as a fulcrum, such that the flow-cell component 120 can be slightly bent along its length, over the connection between the first and second arrays of the electrical connectors 113, 123. That is, in the connected configuration, the front end 121 of the flow-cell component 120 may not be merely passively constrained by the surrounding components, but may be actively urged upwards towards the clip 118. Similarly, the back end of the flow-cell component 120 may also urged upwards against the restraining latch. As a result, when it comes to disconnect the flow-cell from the base component 110, this can be easily achieved by releasing the latch 119, When the latch 119 is released, the back end of the how-cell component 120 springs upwards (due to the fulcrum function of the first array of electrical connectors 113, and the continued force applied to the front end 121 by the clip 118) allowing the flow-cell component 120 to be easily extracted. In addition, the lip of the cantilever 133, which is caught behind the clip 118 prevents the flow-cell component 120 from shooting out of the base component 110 when the latch 119 is released. The cantilever may advantageously be flexible such that it is wider compression when the flow cell is latched and expands when the flow cell component is released, forcing the cantilever against the clip 118, causing the back end of the flow cell to raise up to a more elevated position facilitating easier removal of the flow cell component. Instead, the back end of the flow-cell component 120 pivots upwards when the latch 119 is released, allowing the flow-cell component 120 to be readily extracted.

As will be appreciated from the above discussion, the particular features of the components 110, 120 allow for the relative connection of the first and second array of electrical connectors 113, 123 to be accurately handled with minimum fuss.

The positioning of the walls 114 and the rails 115 at a predetermined position with respect to the first array of electrical connectors 113 contribute to ensuring the correct positioning the y-direction. Preferably, the tolerance between the flow-cell component 120 and the base component 110, at the front and hack ends along the lateral sides 125 and/or along rail reliefs 126, is less than half the pitch between the connectors hi the first and second arrays of electrical connectors 113, 123. Alternatively, the front and/or back ends of the flow-cell component 120 may be designed to be compressible to fit within the width between the parallel lateral walls 114. FIG. 6 illustrates the optional compressible sections 139 at front end 121 of the flow-cell component. Compressible sections 139 may be implemented by springs, for example. If the compressible sections 139 are provided, they are preferably designed so that elastic averaging between the compressible sections leads to the correct location of the flow-cell component in the y-direction.

The provision of the front tips 116 of the rails 115 at a predetermined position with respect to the first array of electrical connectors 113, and the provision of the shoulders 127 on the flow-cell component 120 at a predetermined position with respect to the second array of electrical connectors 123, ensure that the arrays can be correctly aligned in the x-direction also. This is facilitated by the provision of the spring 117 and the front contact point 117, which interact to urge the shoulders 127 against the front tips 116 of the rails 115, and thus ensure that the to arrays of electrical connectors 113, 123 are correctly positioned. Of course, in other arrangements, the urging of the shoulders 127 against the rail tips 26 could be provided by other means. For example, the spring could be provided on the first component 110, instead of the front end 121 of the flow-cell component 120. As already mentioned, the z positioning of the two arrays 113, 123 is ensured by providing a downward force at both ends of the flow-cell component 120, through the clip 118 and the latch 119.

Figure 11:
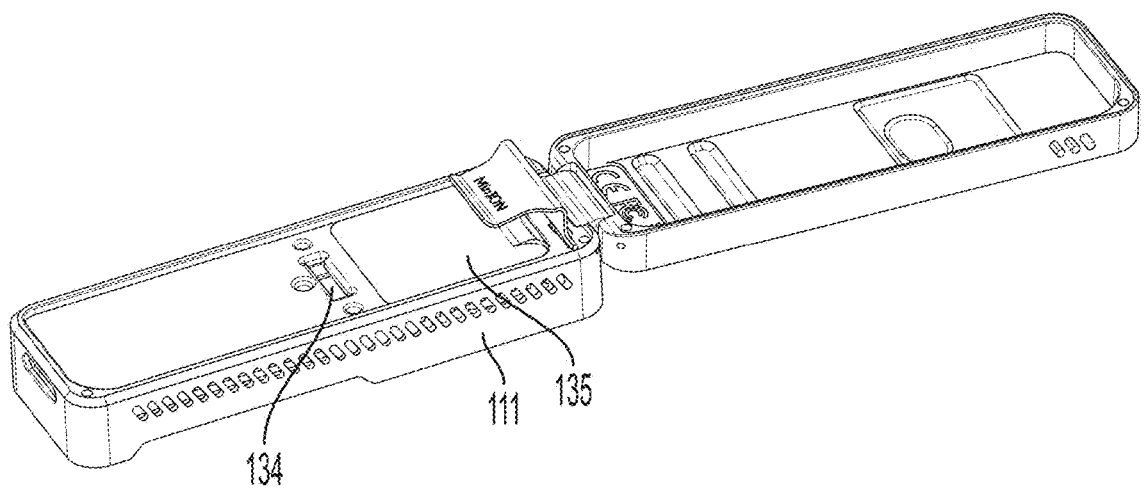
FIG. 11 is a perspective view a first sub-component of the base component of FIG. 5.
Figure 12:
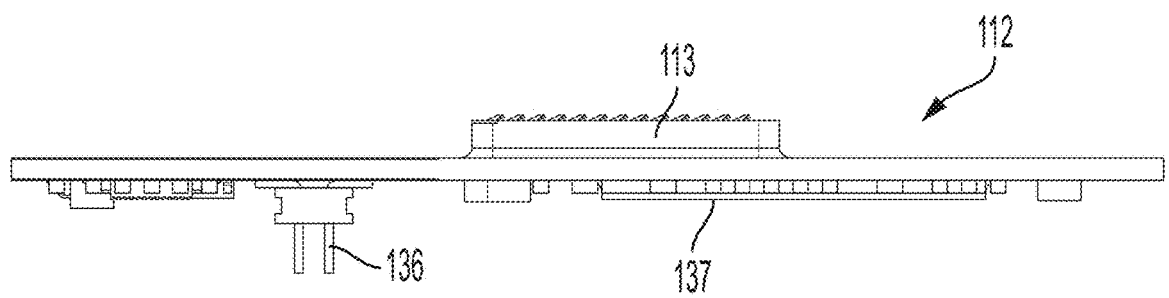
FIG. 12 is a side profile of a second sub-component of the base component of FIG. 5, with the outer walls removed.
Figure 13:
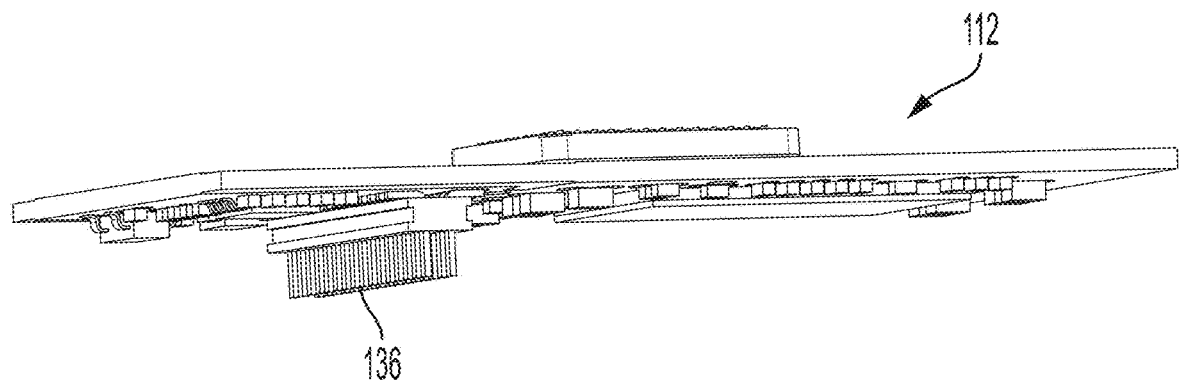
FIG. 13 is an isometric projection of FIG. 12.

As mentioned above, the base component 110 can be constructed of two sub-components 111, 112. FIG. 11 illustrates the first sub-component 111, when disconnected from the second sub component 112. The second sub-component 112 is shown in side view in FIG. 12 (with the surrounding walls 114 and rails 115 removed) and isometric view in FIG. 13, which gives a better view of the array of connector pins 136.

In the particular embodiment shown, the first sub-component 111 houses some of the analysis electronics, and also provides the required cooling capacity. In order to provide a connection between the electronics of the first sub-component 111 and the electronics of the second sub-component 112, a connector socket 134 is provided in first sub-component 111. A heat sink surface 135 is also provided, which is cooled by the cooling component 137 (see FIG. 7).

The second sub-component 112 has a set of connector pins 136 that fit into the connector socket 134 of the first sub-component 111. The connector pins 136 are connected to the electrical connectors in the first array of electrical connectors 113. In this case, the second sub-component 112 includes an ASIC provided beneath first array of electrical connectors 113, and the connector pins 136 are connected to the first array 113 via the ASIC. The ASIC itself has an array of connectors, to which the first array of electrical connectors is (fixedly) connected. However, the first array of electrical connectors 113 may have a different array pitch to that of the ASIC. For example the first array 113 may have a pitch of around whereas the ASIC may have a smaller pitch such as around 250 µm.

The second sub-component 112 has a heat transfer surface 137, for removing heat from the electrical connectors 113. This may be to remove heat generated during connection to the flow-cell component 120, but may also be used to regulate the temperature before a connection is made, to ensure any sensitive components of the flow-cell are not damaged by heat upon connection. The heat is transferred to the heat sink surface 135 on the first sub-component 111. A good heat transfer contact is achieved due to the clip 118 of the first sub-component 111 bearing against the canopies 131 of the second sub-component 112. In other words, the clip 118 urges the second sub-component into contact with the first sub-component 111, thereby ensuring a good contact between the heat transfer surface 137 and the heat sink surface 135.

Figure 14:
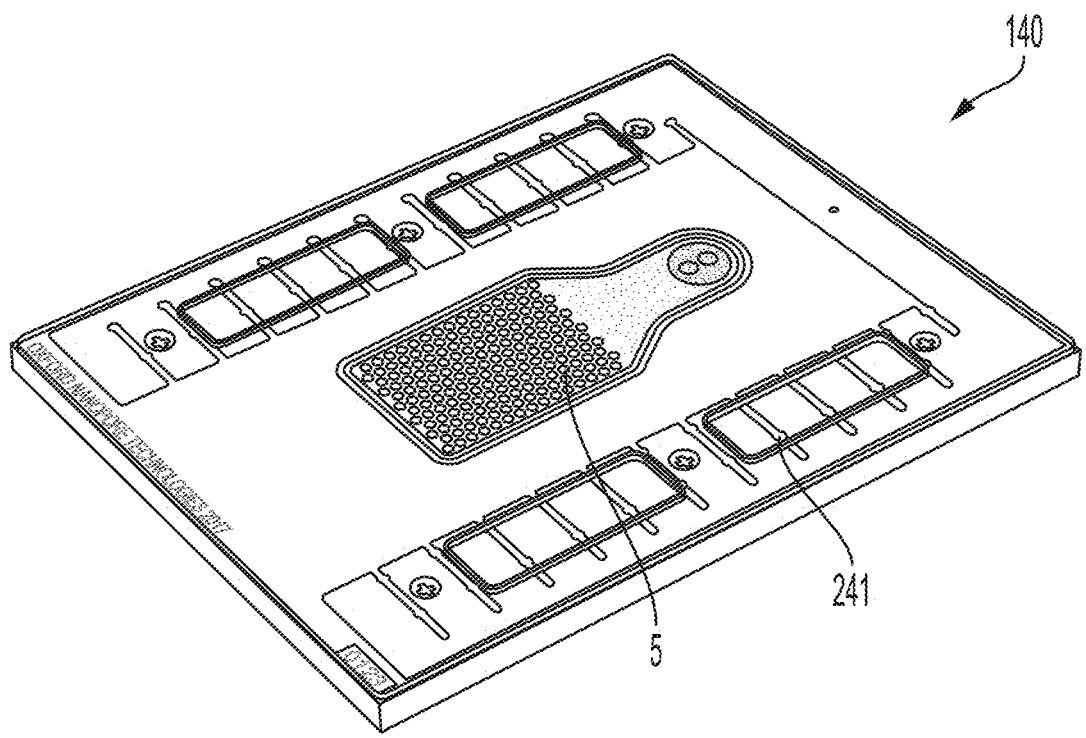
FIG. 14 is a perspective view of a sensor portion of a flow-cell.

FIG. 14 shows a sensor portion 140 of the flow-cell component 120 that provides a sensing array (linking through the second array of electrical connectors 123, on the underside), in this example, the sensing array is an array of wells 5, similar in function to those of FIG. 1.

Figure 15:
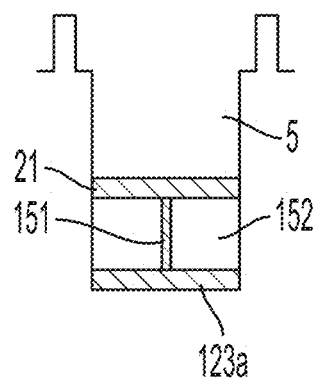
FIG. 15 is a schematic cross section through a sensor well of the sensor in FIG. 14.

Each well is connected through one of the electrical connectors in array 123. FIG. 15 illustrates one possible construction for this, Pad 123a is the underside connector of the well, which forms one of the second array of electrical connectors 123. Pad 123a can be made from any conductive material, such as gold for example. Pad 123a is connected by via 151 to an electrode 21 at the bottom of the well 5. Electrode 21 may be made from any conductive material that is suitable for contacting the contents of the well 5, and may be made from platinum for example. The via 151 is encased in an insulator. In one embodiment the insulator is around 500 μm thick. The insulator can be made of silicon or glass, for example.

Figure 16:
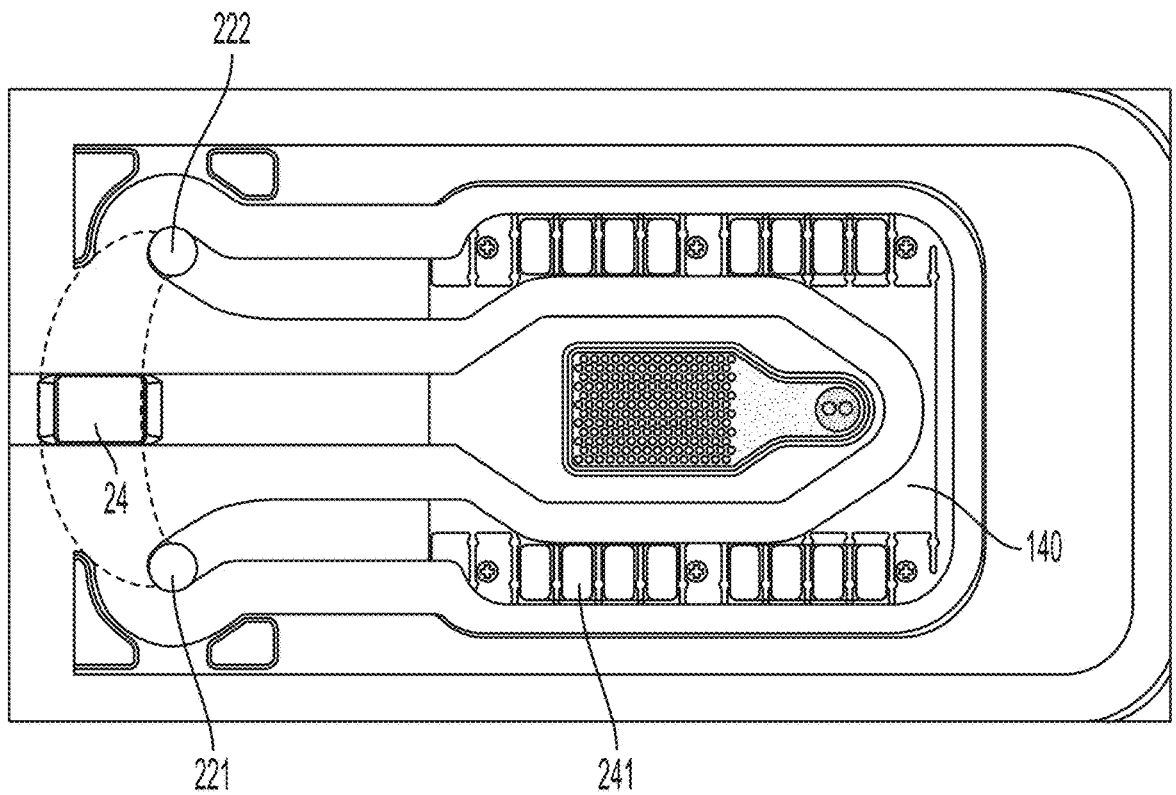
FIG. 16 is a plan view of the sensor of FIG. 14 and the surrounding flow cell.

FIG. 16 shows how the sensing array 140 fits into the surround flow-cell component 120. In particular, a common electrode 241, similar to that of FIG. 1, is provided in the flow-cell component 120 which may serve as a reference electrode. However, in contrast to FIG. 1, the common/counter/reference electrode 241 is not directly in contact with the test liquid passing over the array of wells 5. Instead, four exposed areas of the counter electrode 241 (the precise number is not important) are provided in contact with an ionic solution, that may contain a redox mediator that contacts the electrode 241 and the underside of an ion selective harrier 24, such as a Nation film. The ionic solution (not shown) contacts the underside of the ion selective barrier via ports 221 and 222 connecting fluid channels (shown in dotted lines) to the underside of the barrier and thus providing indirect electrical contact with the test solution and the counter electrode 24. This can help prevent or reduce the reference electrode 24 components or the redox mediator solution from directly interfering with components such as enzymes present in the test solution.

FIGS. 17 to 20 show cross sectional views of the two components 110, 120 as they are connected and disconnected.

Figure 17:
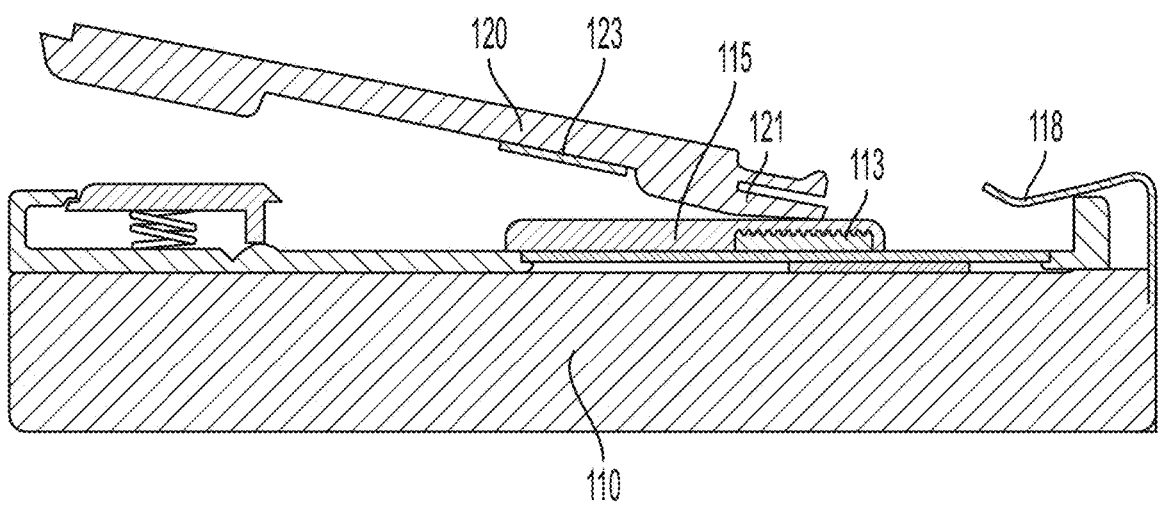
FIG. 17 shows a cross sectional view of two components as they are brought together in preparation for making a connection.

In FIG. 17, it can be seen how the front end 121 of the flow-cell component 120 is prevented from contacting the first array of connectors 113, as it is held aloft by the rails 115. The back end of the flow-cell component 120 is also wide enough that it would be prevented from contacting the first array of connectors 113

Figure 18:
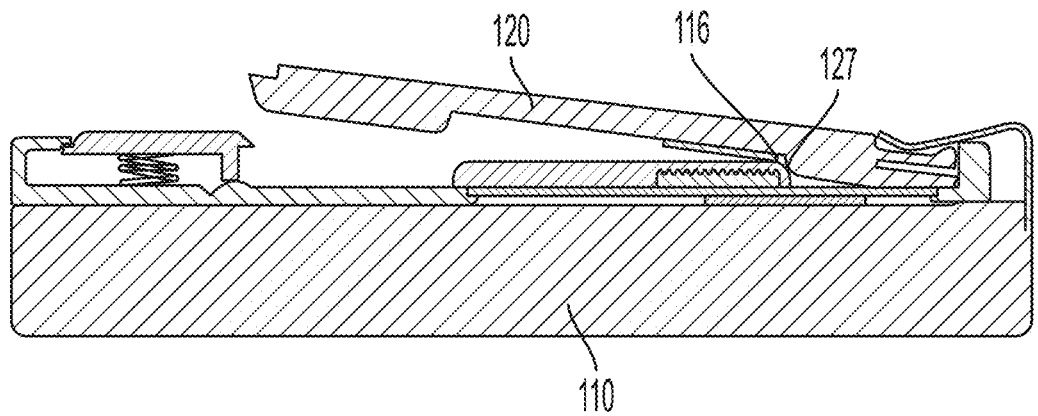
FIG. 18 shows a cross sectional view of two components as they begin to engage with each other.

In FIG. 18, the front end 121 of the flow-cell component 120 is positioned under the clip 118, and the shoulder 127 of the flow-cell component 120 passes over the rail tip 116. The shoulder 127 is then urged hack against the rail tip 116 by the spring force between the front of the flow-cell component and the front wall contact point 117 of the base component 110.

Figure 19:
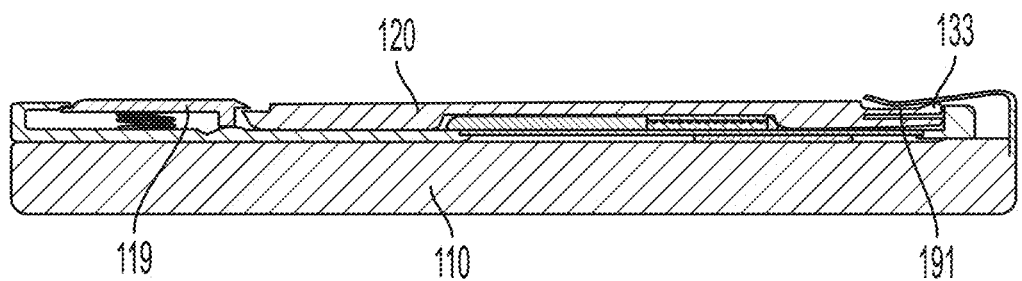
FIG. 19 shows a cross sectional view of two components connected together.
Figure 22:
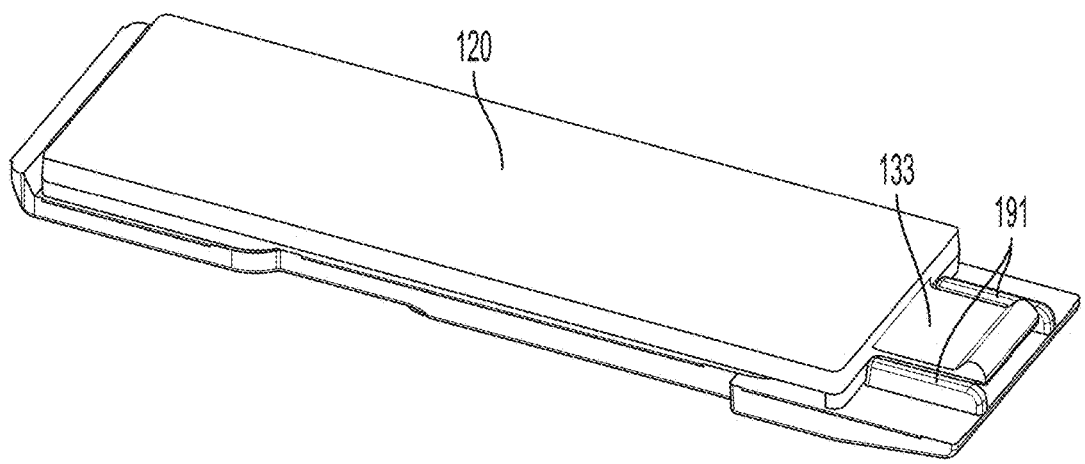
FIG. 22 shows a perspective view of a flow-cell component illustrating fixed contact points either side of the cantilever portion.

In FIG. 19, the flow-cell component 120 is in the connected position, with the latch 119 engaged. The flexible cantilever portion 133 of the front end 121 of the flow-cell component 120 is flexed downwards as it bears against clip 118, until clip 118 comes into contact with fixed contact points 191 on the front end 121. As these are difficult to see hi FIG. 19, the fixed contact points 191 are illustrated in FIG. 22.

Figure 20:
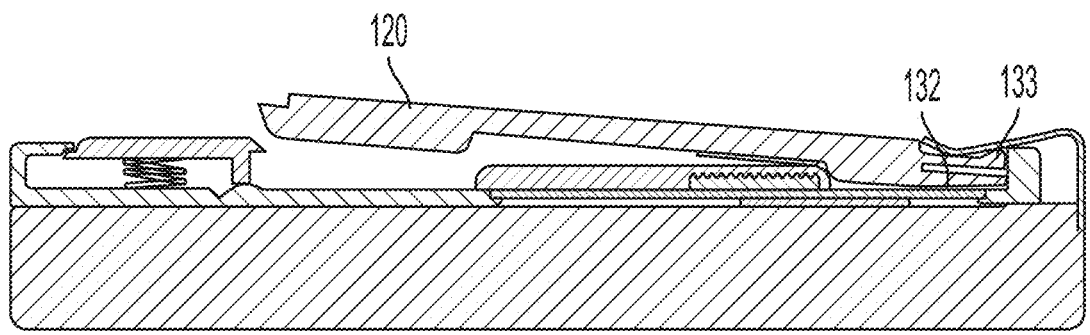
FIG. 20 shows a cross sectional view of two components as they are disengaged.

In FIG. 20, the latch 119 has been disengaged. The cantilever portion 133 of the front end 121 returns from the flexed state, maintaining contact with clip 118, providing additional downward travel of the front end 121. The tapered section 132 contacts the surface of the base portion 110.

Figure 21:
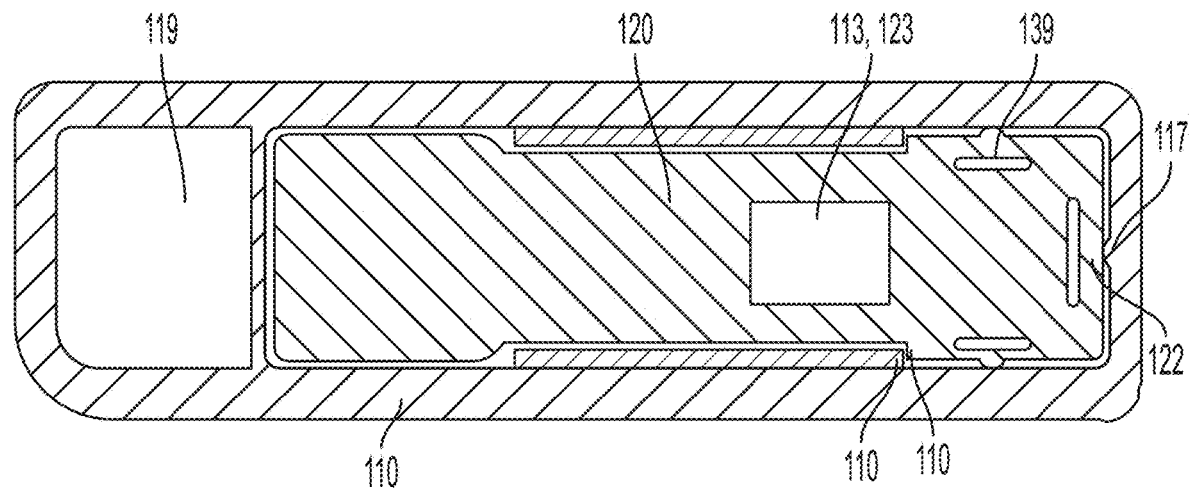
FIG. 21 shows a plan view of two components connected together.

FIG. 21 illustrates an example of the features that assist with aligning the two arrays of the connectors. The shoulder 127 and rail tip 116 act as a datum pair along the length of the components, with the front wring 122 acting to urge the shoulders 127 and rail tips 116 together. The compressible sections 139 (in this example) interact with the walls to act as a datum pair in the width direction. As mentioned above, elastic averaging between the pair of compressible sections 139 can be used to urge the flow-cell component 120 into the correct position in the width direction. Another benefit of the compressible sections 139 is that the lateral sides 125 come into contact with the walls 114 (instead of being at a tolerance distance from them), providing a further damping action when the latch 119 is released, and thus reducing 'twanging' or vibration of the flow-cell component as it is held in the position of FIG. 20, for example. The connector arrays 113, 123 themselves act as the datum pair in the depth direction, with the combination of the latch 119 and the clip 118 acting to urge them together.

Figure 23:
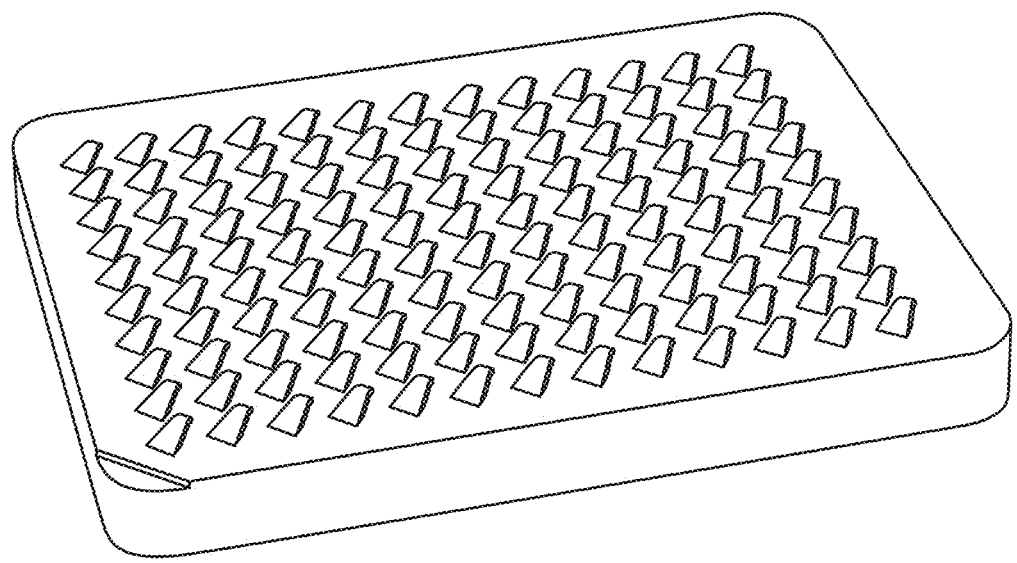
FIG. 23 shows a perspective view of the array of first connectors.
Figure 24:
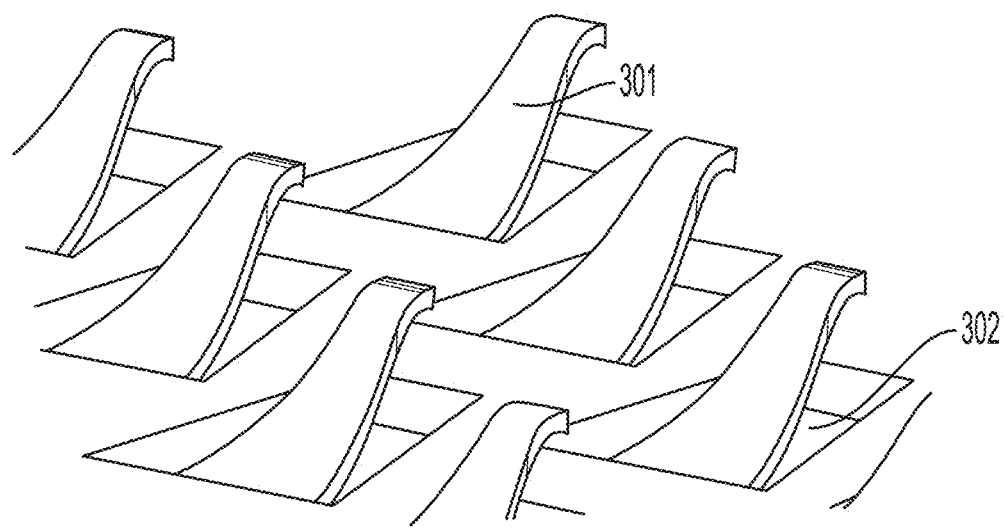
FIG. 24 shows a close up perspective view of the array of first connectors.

FIG. 23 illustrates an example of the first array of connectors 301 with a pitch of 800 um. FIG. 24 shows a close up of the connectors 301 which are sprung loaded and provided in respective recesses 302. To increase their strength each connector tapers outwards towards its base. The connectors are 100 um thick and project to height of 800 um above the recess. The connectors are advantageously sprung loaded and project from the base to facilitate their connection to the second array under an applied force, in contrast to the planar array of second connectors, the first array of connectors is however more prone to being damaged by the flow cell component. Thus the first component is advantageously provided with rails which serve to protect the first array.

The forgoing discussion explains the invention by way of example only, and the skilled reader will appreciate that variations of the specific embodiments are possible within the scope of the attached claims. In particular, the disclosure, in so far as it relates to connecting one component to another, can be applied to any components and not just the specific examples discussed herein.

The invention claimed is:

1. A kit comprising first and second component parts adapted for connection to each other, wherein:
   the first component part comprises:
      a first array of electrical connectors;
      two substantially parallel lateral walls, one provided on either side of the first array of electrical connectors at a predetermined position with respect to the first array of electrical connectors;
      two rails provided between the first array of electrical connectors and the substantially parallel lateral walls, one rail being on either side of the first array of electrical connectors, wherein each rails extends at least along a length of the first array of electrical connectors, and has a front tip positioned at a predetermined position with respect to the first array of electrical connectors;
      a front contact point;
      an overhang for receiving the second component part;
   the second component part comprises:
      a second array of electrical connectors, for connection to the first array of electrical connectors;
      a front end being configured to fit to a width between the substantially parallel lateral walls,
      lateral sides, each comprising a rail relief to allow the lateral sides to fit around the two rails, and wherein a shoulder is formed by the front end of each rail relief;
   and wherein the first and second component parts are configured such that they may be connected by sliding the front end of the second component part along the two rails of the first component part and under the overhang, so that the shoulders of the rail reliefs of the second component part pass the front tips of the rails of the first component part, and the front end of the second component part bears against the front contact point of the first component part, urging the shoulders of the rail reliefs against the front tips of the rails, thereby locating the second array of electrical connectors in the correct position for connecting to the first array of electrical connectors.

2. The kit according to claim 1, wherein the rails of the first component part project above the first array of electrical connectors, such that the second component part cannot be brought into contact with the first array of electrical connectors until the first and second arrays of electrical connectors are aligned in the correct position for connecting.

3. The kit according to claim 1, wherein the front end of the second component part comprises a front spring.

4. The kit according to claim 3, wherein the front spring of the second component part is provided by a flexible portion of the front end of the second component part.

5. The kit according to claim 3, wherein the front contact point of the first component part comprises a pip for the front spring of the second component part to bear against.

6. The kit according to claim 1, wherein a front wall of the first component part comprises a front spring.

7. The kit according to claim 1, wherein a width of the front end and a width of a back end of the second component part are each smaller than the width between the substantially parallel lateral walls by up to half a pitch between electrical connectors of the first array of electrical connectors.

8. The kit according to claim 1, wherein the front end and/or a back end of the second component part are compressible to fit within the width between the substantially parallel lateral walls.

9. The kit according to claim 1, wherein the overhang is a spring.

10. The kit according to claim 1, wherein the first component part has first and second sub-parts, the first and second sub-parts being separable from each other.

11. The kit according to claim 10, wherein the first sub-part comprises the overhang, and the second sub-part comprises: the two substantially parallel lateral walls, the two rails provided between the first array of electrical connectors and the substantially parallel lateral walls, and the front contact point.

12. The kit according to 11, wherein the second sub-part comprises a canopy for fitting against the overhang of the first sub-part.

13. The kit according to claim 1, wherein the first array of electrical connectors is raised from a surface of the first component part, so as to act as a fulcrum over for the second component part.

14. The kit according to claim 13, wherein the first or second component part comprises a latch configured to hold down a back end of the second component part, to hold the first and second component parts in a connected configuration.

15. The kit according claim 14, wherein the overhang, the latch, and the first array of electrical connectors act in combination to bend the second component part when it is held in the connected configuration.

16. The kit according to claim 1, wherein the front end of the second component part further comprises a flexible cantilever for fitting under the overhang of the first component part.

17. A method for connecting first and second component parts to each other, wherein:
the first component part comprises:
a first array of electrical connectors;
two substantially parallel lateral walls, one provided on either side of the first array of electrical connectors at a predetermined position with respect to the first array of electrical connectors;
two rails provided between the first array of electrical connectors and the substantially parallel lateral walls, one rail being on either side of the first array of electrical connectors, wherein each rails extends at least along a length of the first array of electrical connectors, and has a front tip positioned at a predetermined position with respect to the first array of electrical connectors;
a front contact point;
an overhang for receiving the second component part;
the second component part comprises:
a second array of electrical connectors, for connection to the first array of electrical connectors;
a front end and a back end, each configured to fit to a width between the substantially parallel lateral walls,
lateral sides, each comprising a rail relief to allow the lateral sides to fit around the two rails, and wherein a shoulder is formed by the front end of each rail relief;
and the method comprising:
sliding the front end of the second component part beyond the front tips of the two rails of the first component part and under the overhang;
pressing the front end of the second component part against the front contact point of the first component part, so that either the front end or the front contact point undergoes compression, thereby passing the shoulders of the rail reliefs of the second component part beyond the front tips of the rails of the first component part; and
allowing the compression in the front end or the front contact point to urge the shoulders of the rail relief against the front tips of the rails, thereby locating the second array of electrical connectors in the correct position for connecting to the first array of electrical connectors.

18. The method according to claim 17, wherein the rails of the first component part project above the first array of electrical connectors, such that the second component part is prevented from contacting the first array of electrical connectors during the sliding step, until the first and second arrays of electrical connectors are aligned in the correct position for connecting.

19. The method according to claim 17, wherein the front end of the second component part, or the front contact point, comprises a front spring.

20. The method according to claim 17, further comprising compressing the front and/or back ends of the second component part to fit within the width between the substantially parallel lateral walls.

* * * * *